United States Patent
Sugise et al.

(10) Patent No.: US 6,518,461 B2
(45) Date of Patent: Feb. 11, 2003

(54) METHOD OF CONTINUOUSLY PRODUCING A CYCLODODECANONE COMPOUND

(75) Inventors: Ryoji Sugise, Ube (JP); Shuji Tanaka, Ube (JP); Takashi Doi, Ube (JP); Masayuki Nishio, Ube (JP); Sadao Niida, Ube (JP); Tsunao Matsuura, Ube (JP)

(73) Assignee: UBE Industries, Ltd., Ube (JP)

( * ) Notice: Subject to any disclaimer, the term of this patent is extended or adjusted under 35 U.S.C. 154(b) by 0 days.

(21) Appl. No.: 09/981,963

(22) Filed: Oct. 19, 2001

(65) Prior Publication Data

US 2002/0077509 A1 Jun. 20, 2002

(30) Foreign Application Priority Data

Oct. 20, 2000 (JP) .......................................... 2000-320734

(51) Int. Cl.$^7$ ................................................ C07C 45/67
(52) U.S. Cl. ........................ 568/347; 568/350; 568/356
(58) Field of Search ................................. 568/315, 318, 568/322, 347, 350, 356, 375

(56) References Cited

U.S. PATENT DOCUMENTS

| 4,734,529 A | 3/1988 | Berg et al. .................. 568/310 |
| 4,885,397 A | * 12/1989 | Bueschken |

FOREIGN PATENT DOCUMENTS

| DE | 3601380 A1 | 7/1987 | ............ C07C/45/58 |
| DE | 3744094 A1 | 7/1989 | ............ C07C/49/587 |
| DE | 19915894 C1 | 8/2000 | ............ C07C/49/413 |
| EP | 1 125 909 A1 | 8/2001 | ............ C07C/45/58 |
| RU | 407874 | 12/1973 | ............ C07C/49/27 |

OTHER PUBLICATIONS

Zakharkin et al. Zh. Org. Khim. (1990), 26 (7), p. 1497–1500. Isomerization of trans–1,2–epoxy–cis, trans–5, 9–cyclododecadiene . . . to the corresponding ketones under the action of lithium and magnesium bromides and iodides. Abstract.*

* cited by examiner

Primary Examiner—Johann Richter
Assistant Examiner—Sikarl A. Witherspoon
(74) Attorney, Agent, or Firm—Morgan, Lewis & Bockius LLP (57) ABSTRACT

A cyclododecanone compound is continuously produced by an isomerization reaction of a corresponding epoxycyclododecane compound in the presence of a catalyst including lithium bromide and/or lithium iodide, the isomerization reaction being carried out by passing a reaction mixture containing the epoxycyclododecane compound and the catalyst through a continuous reaction apparatus including at least one tubular reactor preferably at a temperature of 100 to 350° C.

9 Claims, 5 Drawing Sheets

METHOD OF CONTINUOUSLY PRODUCING A CYCLODODECANONE COMPOUND

BACKGROUND OF THE INVENTION

1. Field of the Invention

The present invention relates to a method of producing a cyclododecanone compound which is useful as a material for producing laurolactam, dodecanedioic acid and dodecane diol. More particularly, the present invention relates to a process for producing a cyclododecanone compound, for example, cyclododecanone, cyclododecenone, cyclododecadienone or cyclododecatrienone by catalytically isomerizing a corresponding epoxycyclododecane compound, for example, epoxycyclododecane, epoxycyclododecene, epoxycyclododecadiene or epoxycyclododecatriene, with a high conversion of the epoxycyclododecane compound with a high selectivity to the cyclododecanone compound, within a relatively short time.

2. Description of the Related Art

Methods for producing a cyclododecanone by isomerizing a corresponding epoxycyclododecane compound in the presence of a catalyst consisting of a lithium halide are known from a plurality of reports.

For example, German Patent No. 3,744,094 discloses an isomerization of an epoxycyclododecane in the presence of a catalyst consisting of lithium chloride in a reaction medium consisting of N-methylpyrrolidone or N,N'-dimethylethyleneurea to produce cyclododecanone with a yield of 94%.

Also, German Patent No. 3,601,380 discloses that, by isomerization of 1,2-epoxy-5,9-cyclododecadiene in the presence of a catalyst consisting of sodium iodide in a reaction medium consisting of a polyethylene glycol (NaI: 3 wt %, 195° C., 9 hours), cyclododeca-3,7-diene-1-one is produced with a yield of 98.7%.

In each of the above-mentioned methods, however, as a polar solvent is employed as a reaction medium, means for recovering the solvent or for decomposing the solvent must be added to the production system for the target compound and this causes the production cost of the target compound to increase.

Further, the reaction rate of the isomerization reaction is decreased by a dilution effect or a solvation effect of the solvent, and thus the reaction time necessary to effect the isomerization reaction at a conversion close to 100% becomes long. Also, as the reaction is carried out in a batch type reaction system, the above-mentioned methods are unsuitable for industrially producing the target compound in a large quantity with a high efficiency.

Further, SU Patent 407,874 discloses an isomerization reaction of an epoxycyclododecane, in the presence of a catalyst consisting of anhydrous LiBr, in no solvent. In examples of the SU patent, it is reported that, when the reaction was carried out in an amount of LiBr of 4% by weight at a reaction temperature of 120 to 130° C. for a reaction time of 18 hours or in an amount of LiBr of 3.3% by weight at a reaction temperature of 200° C. for a reaction time of 3 hours, the target cyclododecanone was obtained at a yield of 100% or 83.3%.

In the former example, the reaction time is too long, and thus the reaction is not practical, and in the later example, the selectivity to the target compound is low and a by-product having a high boiling temperature was produced. The high boiling temperature by-product is disadvantageous in that when the catalyst is recovered from the reaction mixture after the reaction is completed and recycled to the reaction procedure, the high boiling temperature by-product is accumulated in the reaction system to affect the reaction, and thus an additional procedure for removing the high boiling temperature by-product from the reaction mixture becomes necessary.

In this connection, it may be considered that for the purpose of increasing the reaction rate, the concentration of the catalyst in the reaction system should be increased. However, in the method of the former example, since the solubility of LiBr in the reaction system is saturated, the concentration of the catalyst cannot be increased. In the method of the later example, the reaction temperature is established at a high level to increase the reaction rate. This high temperature causes a side reaction to occur, the yield of the target compound to be decreased, and the high boiling temperature by-product to be produced.

Further, Zh. Org. Khim (1990), 26(7), 1497–1500, discloses that, when an isomerization reaction of an epoxycyclododecane was carried out in the presence of 2.3 molar % of a catalyst consisting of LiBr (lithium bromide) at a reaction temperature of 150° C. for a reaction time of 10 hours, the target cyclododecanone was obtained at a yield of 96.6%, and when the reaction of the epoxycyclododecane was effected in the presence of 1.5 molar % of LiI (lithium iodide) at 150° C. for 5 hours, the target cyclododecanone was obtained at a yield of 91.2%. In the case of this report, however, it is assumed that, to make the conversion of the epoxycyclododecane close to 100%, a very long reaction time is necessary. Also, the reaction of the report was effected in a batch-type reaction system, and thus no continuous method for the reaction is disclosed in the report.

In the case where a cyclododecanone compound is produced by isomerizing an epoxycyclododecane compound, since the boiling temperature of the epoxycyclododecane compound is approximately equal to that of the cyclododecanone compound, there are many cases in which the separation of the two compounds from each other by distillation is very difficult from an industrial point of view. Also, since the two compounds are similar, in physical and chemical properties, to each other, the separation on refining of the two compounds by crystallization or extraction is difficult. Therefore, to produce the cyclododecanone compound with a high degree of purity, it is necessary that the conversion of the epoxycyclododecane compound is controlled to approximately 100%. For this purpose, it is possible to increase the reaction temperature or the content of the catalyst.

However, as mentioned above, an increase in the reaction temperature causes frequent occurrence of side reactions and thus the production of the high boiling temperature compounds is promoted and the yield of the target cyclododecanone compound is reduced.

On other hand, as a measure to enhance the conversion of the epoxycyclododecane compound, it is possible to increase the content of the catalyst in the reaction system. However, the increase in the catalyst content may cause a difficulty in the dissolution of the catalyst in the reaction system and may make the cost of the reaction increase. Thus, this measure is not practical.

All of the reaction procedures of the above-mentioned prior arts are carried out in batch type reactor systems and thus are disadvantageous in that the process operations are complicated, the safety of the operations is unsatisfactory and the operation cost is high. In fact, the isomerization reaction is an exothermic reaction. Therefore, when the cyclododecanone compound is industrially produced in a large quantity by the batch type reactor system, a large amount of heat is generated. In practice, it is important to remove the heat with a high efficiency. For example, when a large amount of an epoxycyclododecane compound is catalytically isomerized at a temperature of 200° C. in a batch type reactor, since the removal of the generated reaction heat is difficult, the reaction temperature may be rapidly increased to such an extent that bumping of the liquid reaction mixture occurs.

As mentioned above, in the conventional technology, it has not yet been possible to isomerize the epoxycyclododecane compound in a short reaction time at a conversion of the compound of approximately 100% with a selectivity to the target compound of approximately 100%. Further, since the known isomerization method is carried out in a batch type reactor, the target cyclododecanone compound cannot be continuously and safely provided. Namely, a continuous process for producing the cyclododecanone compound in an industrial scale has not yet been established.

SUMMARY OF THE INVENTION

An object of the present invention is to provide a process for continuously producing a cyclododecanone compound in an industrial scale by an isomerization reaction of an epoxycyclododecane compound in the presence of a catalyst comprising lithium bromide and/or lithium iodide, in a relatively short reaction time, with a high conversion of the epoxycyclododecane compound, with a high selectivity to the target cyclododecanone compound and with high safety.

The above-mentioned object can be attained by the process of the present invention for continuously producing a cyclodoecanone compound.

The method of the present invention for continuously producing a cyclododecanone compound, comprises isomerizing an epoxycyclododecane compound in the presence of a catalyst comprising at least one member selected from the group consisting of lithium bromide and lithium iodide, wherein the isomerization reaction is continuously carried out by passing a reaction mixture comprising the epoxycyclododecane compound and the catalyst through a continuous reaction apparatus comprising at least one tubular reactor.

In the method of the present invention for continuously producing a cyclododecanone compound, the epoxycyclododecane compound is preferably selected from saturated and unsaturated cyclichydrocarbon compounds having 12 carbon atoms and an epoxy group.

In the method of the present invention for continuously producing a cyclododecanone compound, the epoxycyclododecane compound is preferably selected from epoxycyclododecane, epoxycyclododecenes, epoxycyclododecadienes and epoxycyclododecatrienes.

In the method of the present invention for continuously producing a cyclododecanone compound, the continuous reaction apparatus preferably further comprises at least one vessel type reactor connected to the tubular reactor in series.

In the method of the present invention for continuously producing a cyclododecanone compound, the catalyst preferably comprises lithium iodide.

In the method of the present invention for continuously producing a cyclododecanone compound, the catalyst is preferably present in an amount of 0.01 to 20 molar % based on the molar amount of the epoxycyclododecane compound.

In the method of the present invention for continuously producing a cyclododecanone compound, the isomerization reaction is preferably carried out in an inert gas atmosphere comprising at least one member selected from the group consisting of helium, neon, argon, hydrogen, nitrogen, methane and ethylene gases.

In the method of the present invention for continuously producing a cyclododecanone compound, the isomerization reaction is preferably carried out at a temperature of 100 to 350° C.

In the method of the present invention for continuously producing a cyclododecanone compound, the isomerization reaction is preferably carried out in a nonreactive gas atmosphere comprising at least one member selected from the group consisting of helium, neon, argon, hydrogen, nitrogen, methane and ethylene gases.

In the method of the present invention for continuously producing a cyclododecanone compound, the isomerization reaction is preferably carried out at a temperature of 100 to 190° C. until the conversion of the epoxycyclododecane compound in the reaction mixture reaches a level of 90 molar % or more, and thereafter at a temperature of 190° C. to 350° C.

DESCRIPTION OF THE PREFERRED EMBODIMENTS

In the method of the present invention, to produce a cyclododecanone compound, an epoxycyclododecane compound is subjected to an isomerization reaction in the presence of a catalyst comprising at least one member selected from the group consisting of lithium bromide and lithium iodide, and the isomerization reaction is continuously carried out by passing a reaction mixture comprising the epoxycyclododecane compound and the catalyst through a continuous reaction apparatus comprising at least one tubular reactor.

The epoxycyclododecane compound usable as an starting compound for the method of the present invention is preferably selected from saturated and unsaturated cyclic hydrocarbon compounds having 12 carbon atoms and attached with an epoxy group. Particularly, the epoxycyclododecane compound usable of the present invention is preferably selected from epoxycyclododecane, epoxycyclododecenes, epoxycyclododecadienes and epoxycyclododecatrienes, more preferably from the epoxycyclododecane and epoxycyclododecadienes, still more preferably from the epoxycyclododecane. With respect to the epoxycyclododecane compounds usable for the present invention, there are various isomers usable for the present invention and there is no limitation to the positions of the epoxy group and the double bonds. Also, the isomers include cis-type and trans-type compounds.

Also, the epoxycyclododecane compounds may be subjected alone or in a mixture of two or more thereof to the method of the present invention.

The cyclododecanone compounds to be produced as target products of the method of the present invention are those corresponding to the epoxycyclododecane compounds used as starting compounds for the method of the present invention and particularly include cyclododecanone, cyclododecenones, cyclododecadienones and cyclododecatrienones.

The catalyst for the isomerization reaction of the epoxycyclododecane compounds in accordance with the method of the present invention, comprises at least one member of lithium bromide and lithium iodide. No specific pretreatment for the catalyst is necessary. The lithium bromide and/or lithium iodide available in the trade can be used for the method of the present invention without pre-treatment. The lithium bromide and lithium iodide include anhydrous lithium bromide, lithium bromide monohydrate, lithium bromide dihydrate, lithium bromide trihydrate, anhydrous lithium iodide, lithium iodide monohydrate, lithium iodide dihydrate and lithium iodide trihydrate.

In the method of the present invention, the catalyst may be continuously fed in the state of solid or in the state of a solution of the catalyst in the starting compound, namely the epoxycyclododecane compound or in the product compound, namely the cyclododecanone compound, into a reactor for the isomerization reaction. Alternatively, the catalyst comprising lithium bromide and/or lithium iodide may be continuously fed in the state of an aqueous solution thereof into the reactor. Preferably, the catalyst is dissolved in the epoxycyclododecane compound and/or the cyclododecanone compound and the resultant catalyst solution is continuously fed into a tubular reactor-containing continuous reaction apparatus.

There is no limitation to the amount of the catalyst to be fed into the isomerization reaction. The feed amount of the catalyst is established in consideration of the solubility of the catalyst in the reaction mixture and the reaction conditions. Preferably, the catalyst is fed in an amount of 0.01 to 20 molar %, more preferably 0.1 to 5 molar % per mole of the epoxycyclododecane compound. If the feed amount of the catalyst is too small, the time necessary to complete the isomerization reaction may be too long and thus an industrial disadvantage occurs. Also, if the feed amount of the catalyst is too high, it causes the reaction cost to be too high and thus an industrial disadvantage occurs.

In the method of the present invention, it is essential that the continuous catalytic isomerization reaction of the epoxycyclododecane compound is carried out by using a continuous reaction apparatus comprising at least one tubular reactor. The tubular-reactor-containing continuous reaction apparatus enables the method of the present invention for producing the cyclododecanone compound from the corresponding epoxycyclododecane compound to be continuously carried out at a high reaction rate, namely within a short time, at a high conversion of the epoxycyclododecane compound at a high selectivity to the cyclododecanone compound and with a high reaction stability in a large industrial scale.

In the method of the present invention, the tubular reactor-containing continuous reaction apparatus is not limited to a specific type of reaction apparatus, as long as the reaction apparatus enables the isomerization reaction for the method of the present invention to be effected. For example, the reaction apparatus may be selected from the apparatuses as shown in FIGS. 1 and 2.

Figure 1:
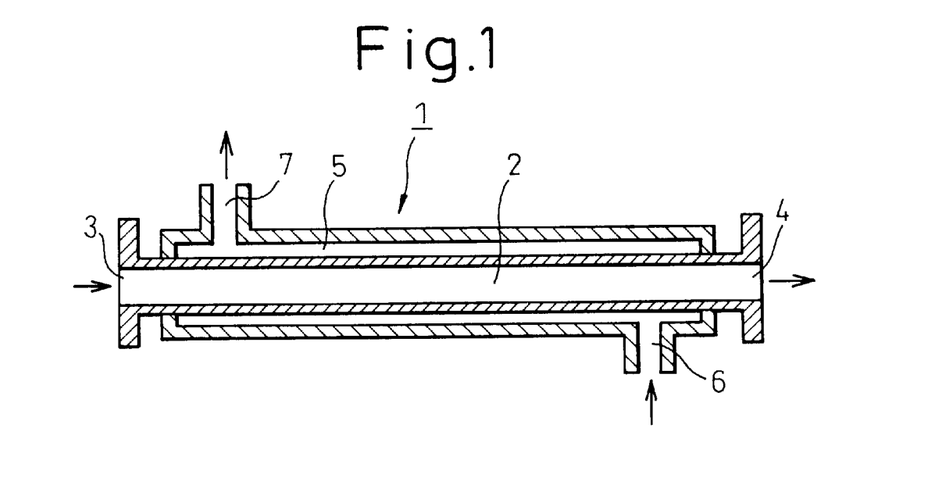
FIG. 1 shows an explanatory cross-sectional profile of a single tube-type reactor which is an example of tubular reactors usable for the method of the present invention.

Referring to FIG. 1, a single tube-type reactor 1 comprises a single straight tube 2 having an inlet 3 and an outlet 4 for a reaction mixture and a heating jacket 5 surrounding the periphery of the tube 2 and having an inlet 6 and outlet 7 for a heating medium. A reaction mixture comprising a starting compound and catalyst is introduced from a supply source (not shown in FIG. 1) into the single straight reaction tube 2 through the inlet 3, and heated to a desired temperature by the heating medium introduced into the heating jacket 5 through the inlet 6 and delivered from the jacket 5 through the outlet 7, to cause the starting compound to be catalytically isomerized into the target compound, and the resultant reaction mixture is delivered from the reactor tube 2 through the outlet 4.

Figure 2:
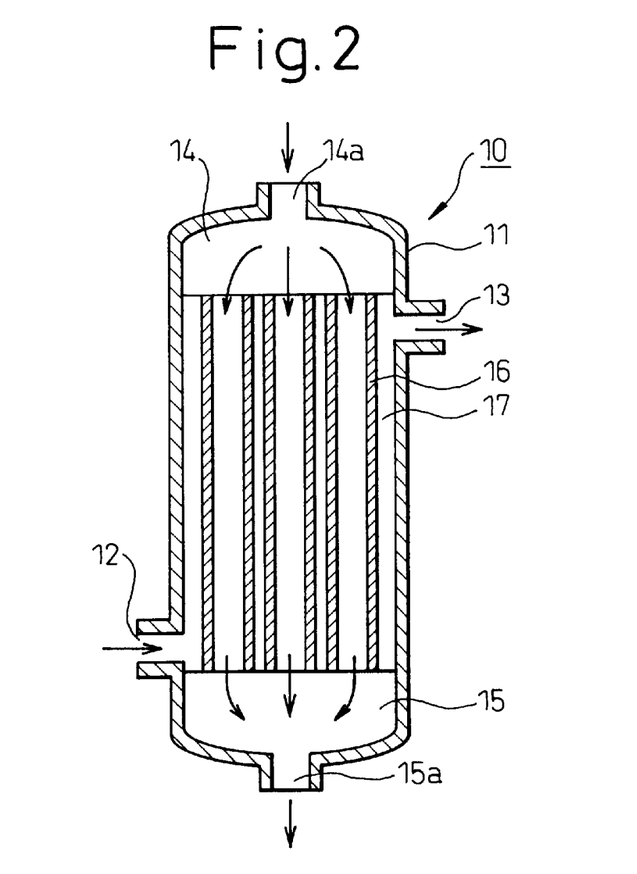
FIG. 2 shows an explanatory cross-sectional profile of a multi-tube-type reactor which is an example of tubular reactors usable for the method of the present invention.

Referring to FIG. 2, a multi-tubular type reactor 10 comprises an outer drum 11 having an inlet 12 and an outlet 13 for a heating medium, an upper chamber 14 formed in an upper inside portion of the drum 11 and having an inlet 14a for a starting reaction mixture, a lower chamber 15 formed in a lower inside portion of the drum 11 and having an outlet 15a for a resultant reaction mixture, a plurality of straight tubes 16 through which the upper chamber 14 and the lower chamber 15 are connected to each other, and a heating medium path 17 formed between the upper and lower chambers 14 and 15 and the plurality of straight tubes 16 through which path the inlet 12 and the outlet 13 for the heating medium are connected to each other.

In FIG. 2, a starting mixture is introduced from a supply source (not shown in FIG. 2) into the upper chamber 14 through the inlet 14a, is distributed into the plurality of straight tubes 16, falls through the straight tubes 16, is collected in the lower chamber 15 and is then delivered through the outlet 15a. Separately, a heating medium is introduced into the heating medium path 17 through the inlet 12 to heat the reaction mixture falling thorough the straight tubes 16 to a desired temperature, and delivered from the path 17 through the outlet 13.

In the reaction apparatuses shown in FIGS. 1 and 2, the reaction mixture and the heating medium flow in opposite directions to each other. However, they may flow in the same direction. There is no limitation to the type of the tubular reactor. A usual tubular reactor, through which a liquid reaction feed can pass, may be used for the present invention. There is no limitation to the cross-sectional profile of the individual tubes of the tubular reactor. The cross-sectional profile is preferably selected from polygonal, oval and circular cross-sectional profiles, more preferably circular cross-sectional profiles.

There is no limitation to the length and the inside diameter (or inside radius) of the tubular reactor. The length and inside diameter of the tubular reactor can be established in response to the temperature and flow rate of the reaction mixture and the type and concentration of the catalyst in the reaction mixture, preferably so that the residing time of the reaction mixture in the tubular reactor is not more than 10 hours, more preferably is 0.1 to 7 hours.

The ideal state of the reaction mixture passing through the tubular reactor is a plug flow. However, in practice, the ideal flow state cannot be realized. There is no limitation to the flow state of the reaction mixture through the tubular reactor.

There is no limitation to the type of the material from which the tubular reactor is formed. For example, a glass or stainless steel tube may be used for the tubular reactor for the method of the present invention.

Figure 3:
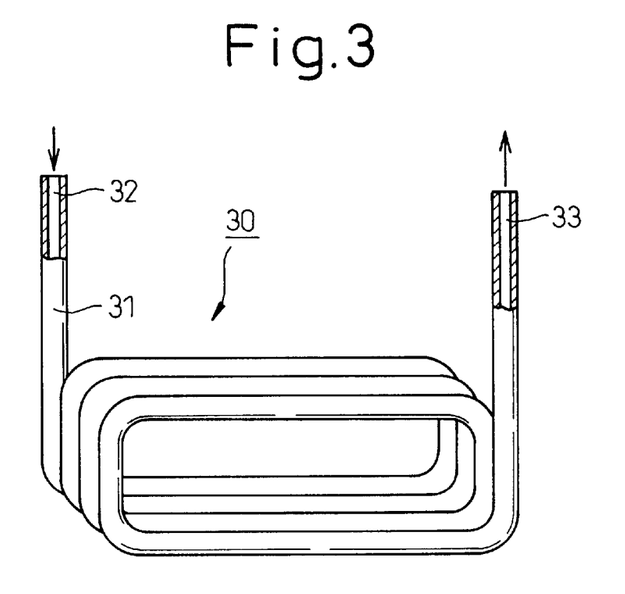
FIG. 3 is an explanatory schematic view of an example of coiled tube-type reactors usable for the method of the present invention.

FIG. 3 shows an explanatory schematic and partially cross-sectional view of an example of a coiled tube-type reactor usable for the method of the present invention. In FIG. 3, a spiral tubular reactor 30 comprises a length of a coiled tube 31 having an inlet 32 and an outlet 33. At least the spirally wound portion of the tube 31 may be immersed in a heating bath or box (not shown in FIG. 3 or may be surrounded by a heating jacket having heating medium inlet and outlet (not shown in FIG. 3).

Referring to FIG. 3, a starting reaction mixture is introduced from a supply source (not shown in FIG. 3) into the coiled tube 31 through the inlet 32, passing through the coiled tube 31 while being heated to a desired temperature by a heating bath, box or jacket (not shown in FIG. 3), and delivered from the tube through the outlet 33.

Figure 4:
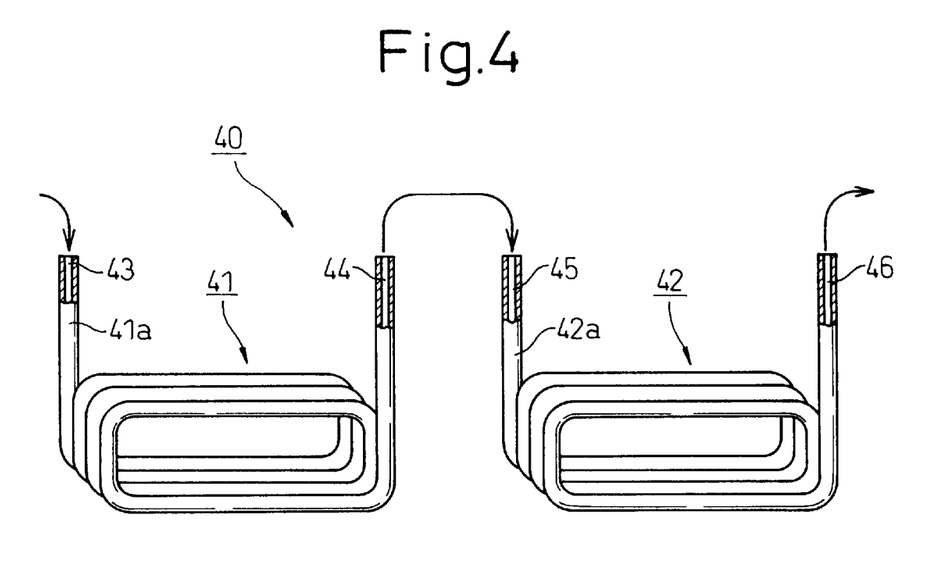
FIG. 4 is an explanatory schematic view of another example of coiled tube-type reactors usable for the method of the present invention.

FIG. 4 shows an explanatory schematic and partially cross-sectional view of another example of a coiled tube-type reactor usable for the method of the present invention.

In FIG. 4, a reaction apparatus 40 comprises two coiled tube-type reactors 41 and 42 connected in series to each other. The front reactor 41 comprises a coiled tube 41a having an inlet 43 and an outlet 44, and the rear reactor 42 comprises a spirally wound tube 42a having an inlet 45 and an outlet 46. The outlet 44 of the front reactor 41 is connected to the inlet 45 of the rear reactor 42 through a connector (not shown in FIG. 4). Also, at least the spirally wound portions of the front reactor 41 and the rear reactor 42 are heated separately from each other with heating baths, boxes or jackets or together with a single heating bath, box or jacket. In the former case, the temperature of a portion the reaction mixture passing through the front reactor 41 can be controlled separately from that of another portion of the reaction mixture passing through the rear reactor 42. In the latter case, the portions of the reaction mixture passing through the front and rear reactors 41 and 42 can be heated to the same temperature as each other.

In the method of the present invention, the reaction apparatus optionally contains at least one vessel type reactor combined with the at least one tubular reactor in series. In this type of reaction apparatus, the starting reaction mixture is introduced into the at least one tubular reactor in which a portion of the epoxycyclododecane compound in the reaction mixture is catalytically isomerized and then into the at least one vessel type reactor in which the remaining portion of the epoxycyclododecane compound is catalytically isomerized to obtain the target cyclododecanone compound with a high conversion of the starting epoxycyclododecane compound with a high selectivity to the target cyclododecanone compound. Alternatively, the starting reaction mixture is introduced into the at least one vessel type reactor and then into the at least one tubular reactor to obtain the target cyclododecanone compound with a high conversion of the starting epoxycyclododecane compound with a high selectivity to the target cyclododecanone compound.

There is no limitation to the type, form and dimensions of the vessel type reactors. Two examples of the vessel type reactors usable for the method of the present invention are shown in FIGS. 5 and 6.

Figure 5:
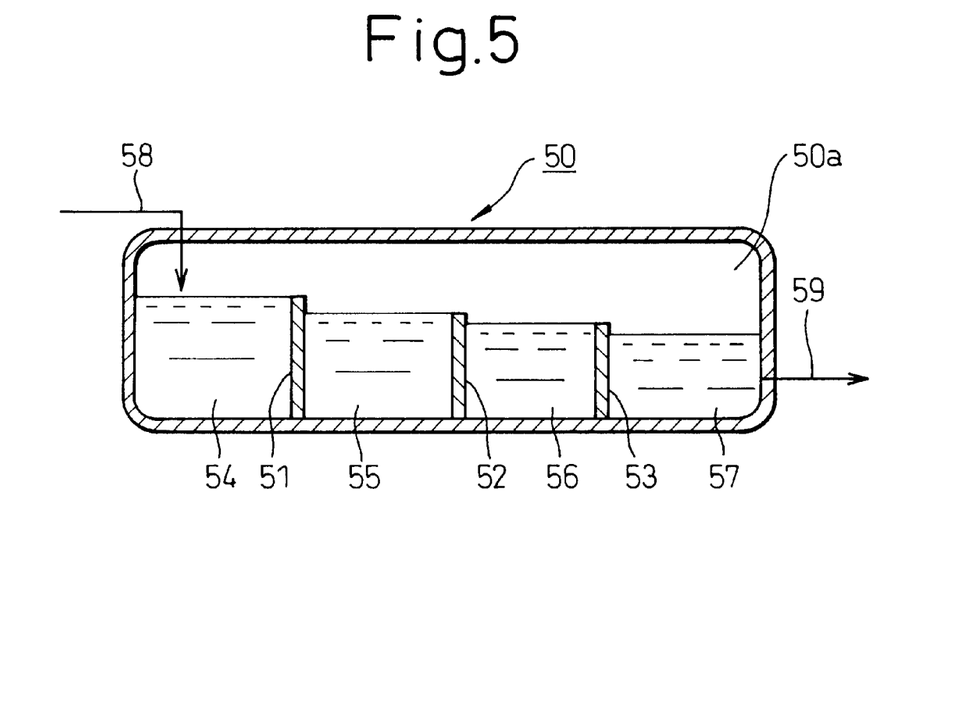
FIG. 5 shows an explanatory cross-sectional profile of an example of vessel-type reactors which may be used in combination with the tubular reactors for the method of the present invention.
Figure 6:
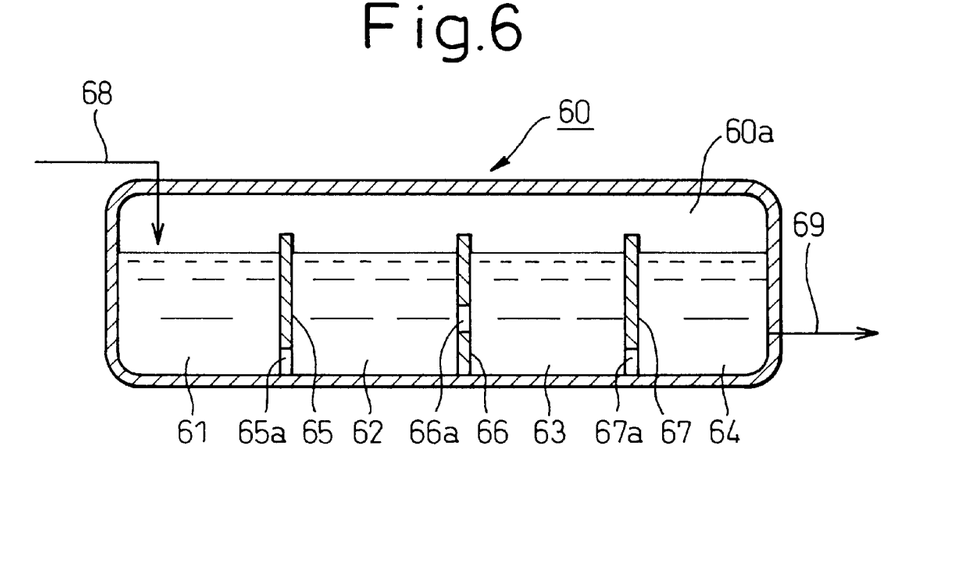
FIG. 6 shows an explanatory cross-sectional profile of another example of vessel-type reactors which may be used in combination with the tubular reactors for the method of the present invention.

In FIG. 5, a closed reaction vessel 50 is divided with partitions 51, 52 and 53 into a plurality of reaction chambers, for example, 4 reaction chambers 54, 55, 56 and 57, forming reaction regions. The frontmost chamber 54 is connected to a feed line 58 for feeding a starting liquid reaction mixture from a supply source (not shown), and the rearmost chamber 57 is connected to a delivery line 59 for delivering the resultant liquid reaction mixture containing the target compound. The top of the partition 51 is higher than the top of the partition 53. Thus, the reaction mixture fed into the frontmost chamber 54 through the feed line 58 successively passes through the reaction chambers 54, 55, 56 and 57, while overflowing over the tops of the partitions 51, 52 and 53, and is finally delivered from the rearmost chamber 57 through the delivery line 59. The space 50a of the reactor 50 above the liquid levels of the reaction chambers 54 to 57 may be filled with an inert gas to seal the reactor 50.

Namely, between a pair of reaction chambers adjacent to each other and separated from each other with a partition, a liquid path over the top of the partition is formed. The liquid path may be formed by a trough, a gutter or a pipe extending over the top of the partition.

In the reactor shown in FIG. 5, each of the partitions 51 to 53 may have at least one hole which can allow the liquid reaction mixture to pass therethrough at a total flow rate lower than the feed rate of the reaction mixture.

In still another embodiment of the vessel type reactor, the reactor has a plurality of reaction chambers separated from each other with partitions arranged between the reaction chambers and connected to each other in series through at least one hole formed in each of the partitions. In this embodiment, a reactor as shown in FIG. 6 can be used. In FIG. 6, the inside of the reactor 60 is partitioned into a plurality of reaction chambers to, for example, form chambers 61, 62, 63 and 64, with partitions 65, 66 and 67 each having at least one of the holes 65a, 66a and 67a through which the reaction chambers are connected to each other. The holes of the partitions form liquid paths. The partitions may be formed by perforated plates. The frontmost chamber 61 is connected to a feed line 68 through which a starting reaction mixture is fed from a supply source (not shown) into the frontmost chamber 61. Also, the rearmost chamber 64 is connected to a delivery line 69 through which a resultant liquid reaction mixture containing a target compound is delivered from the rearmost chamber 64 to the outside of the reactor 60.

The liquid reaction mixture is fed into the frontmost chamber 61 through the feed line 68, successively passes through the separate reaction chambers 61 to 64 while passing through the holes 65a to 67a of the partitions 65 to 67, and the resultant liquid reaction mixture is delivered from the rearmost reaction chamber 64 through the delivery line 69.

In the reactor 60 of FIG. 6, the partitions may be the same, or different, in height as long as each reaction chamber has a satisfactory capacity for the reaction mixture.

In the reactor 60 of FIG. 6, the space 60a above the liquid levels of the reaction chambers 61 to 64 may be filled with an inert gas to seal the reactor 60.

In the vessel-type reactor usable for the present invention, there is no limitation to the number of the reaction regions.

The number of the reaction regions may be 1 to 30, more preferably 3 to 10.

Also, in the vessel-type reactor usable for the present invention, optionally, the reaction mixture is forcedly stirred in at least one reaction region by using a stirrer, a liquid circulation pump or a gas-bubbling means, or is gently stirred by the flow of the reaction mixture through the reaction regions or by a convection current in the reaction mixture, in each region.

The reactor may be heated by a conventional heating means, for example, a heating jacket through which a heating medium circulates.

Figure 7:
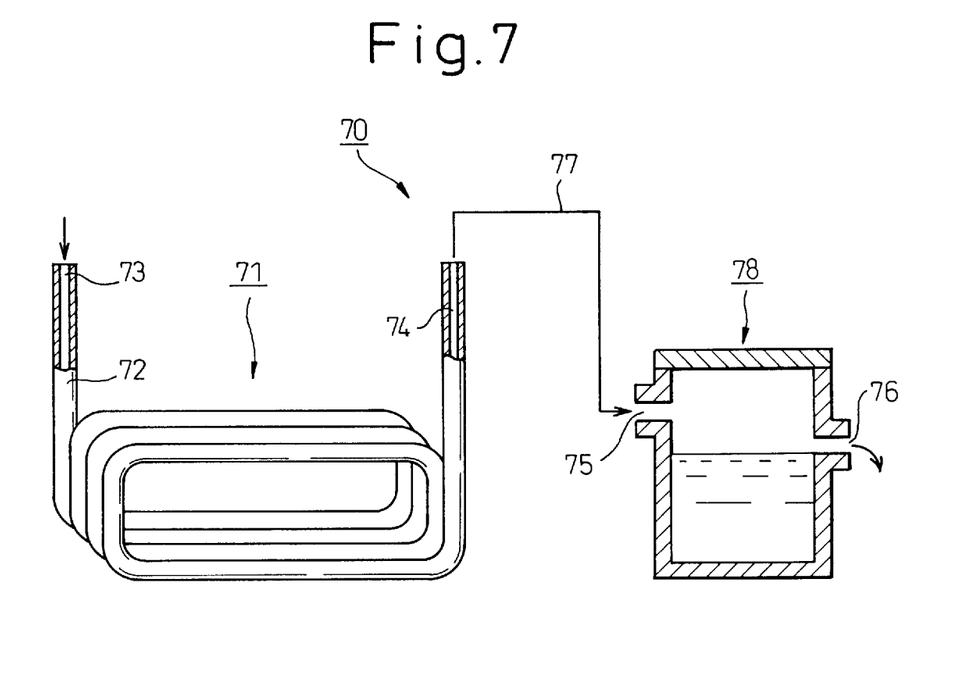
FIG. 7 is an explanatory schematic partial cross-sectional view of a reaction apparatus usable for the present invention.

In an embodiment of the reaction apparatus usable for the method of present invention as shown in FIG. 7, the reaction apparatus 70 comprises a tubular reactor 71 and a closed vessel-type reactor 78 connected in series to each other. In FIG. 7, the tubular reactor 71 is formed from a coiled tube 72 having an inlet 73 and an outlet 74 for a reaction mixture. The inlet 73 is connected to a supply source (not shown) of a reaction mixture. The closed vessel type reactor 78 has an inlet 75 and an outlet 76 for the reaction mixture, and the inlet 75 of the vessel type reactor 78 is connected to the outlet 74 of the tubular reactor 71 through a connecting line 77. The tubular reactor 71 and the vessel type reactor 78 are heated separately from each other or together with each other by a heating means, for example, a heating bath, box or jacket (not shown in FIG. 7) to a desired temperature.

Referring to FIG. 7, a starting reaction mixture is introduced into the coiled tube-type reactor 71 through the inlet 73 and passes through the coiled tube 72 while being heated to a desired temperature for a desired residing time, the reaction mixture is delivered from the coiled tube-type reactor 71 through the outlet 74 and is introduced into the closed vessel-type reactor 78 through the connecting line 77 and the inlet 75, the introduced reaction mixture in the vessel type reactor 78 is heated to a desired temperature for a desired residing time, and the resultant reaction mixture is delivered from the vessel-type reactor 78 through the outlet 76.

There is no limitation to the type of gas atmosphere in which the isomerization reaction is carried out. Preferably, the isomerization reaction is carried out in a nonreactive atmosphere. The non-reactive gas atmosphere preferably comprises at least one member selected from helium, neon, argon, hydrogen, nitrogen, methane and ethylene gases, more preferably from nitrogen and argon gases. The above-mentioned nonreactive gases may be used alone or in a mixture of two or more thereof.

In the method of the present invention the reaction temperature is preferably controlled in the range of from 100 to 350° C., more preferably from 120 to 300° C., still more preferably from 150 to 250° C., further preferably from 160 to 240° C.

If the reaction temperature is lower than 100° C., the reaction may be carried out at too low a reaction rate which is unsuitable for industrial practice. Also, if the reaction temperature is higher than 350° C., the resultant reaction product may contain an impurity having a high boiling temperature in an increased content. Thus, the high temperature reaction is not suitable for industrial practice.

The reaction temperature may locally vary in the tubular reactor-containing reaction apparatus. For example, in a front portion of the reaction apparatus in which the reaction mixture has a high content of the epoxycyclododecane compound, the reaction temperature is controlled to a lower level, and in a rear portion of the reaction apparatus in which the reaction mixture exhibits a conversion of epoxycyclododecane component of 90 molar % or more, the reaction temperature is controlled to a higher level to cause the conversion of the epoxycyclododecane compound to reach about 100 molar %. By controlling the reaction temperature in the above-mentioned way, the target cyclododecanone compound can be obtained at a high selectivity. Particularly, the isomerization reaction is preferably carried out at a temperature of 100 to 190° C. until the conversion of the epoxycyclododecane compound reaches a level of 90 molar % or more, more preferably 95 molar % or more.

Alternatively, the isomerization reaction is carried out at a temperature of 100 to 190° C. until the conversion of the epoxycyclododecane compound in the reaction mixture reaches a level of 90 molar % or more, and thereafter at a temperature of 190° C. to 350° C.

The reasons for the enhancement of the selectivity to the target cyclododecanone compound has not yet been made fully clear. It is assumed that since the resultant cyclododecanone compound has a higher heat stability at a high temperature of more than 190° C. than that of the starting epoxycyclododecane compound, the degree of deterioration of the epoxycyclododecane compound can be decreased by increasing the temperature of the reaction mixture to a high level of more than 190° C. after the content of the epoxycyclododecane compound in the reaction mixture decreases to a low level.

In the method of the present invention, there is no limitation to the reaction pressure of the isomerization reaction. Namely, the isomerization reaction can be carried out at a pressure equal to, or higher or lower than, the atmospheric pressure.

In the method of the present invention, the reaction time is variable in response to the type and content of the catalyst and the reaction temperature. Usually, a reaction time of not more than 15 hours is practically sufficient for the isomerization reaction in accordance with the method of the present invention.

The isomerization reaction in accordance with the method of the present invention is usually carried out without using a reaction medium, because the starting epoxycyclododecane compound and the resultant cyclododecanone compound serve as a reaction medium. However, the reaction may be carried out in a reaction medium consisting of a non-polar solvent.

The non-polar solvent is preferably selected from cyclic hydrocarbons having 6 to 12 carbon atoms. The non-polar solvent can be used in a content of not more than the content of the epoxycyclododecane compound in the starting reaction mixture.

In the method of the present invention using the tubular reactor-containing reaction apparatus, a starting reaction mixture comprising an epoxycyclododecane compound and a catalyst comprising lithium bromide or lithium iodide is continuously introduced into the tubular reactor-containing reaction apparatus, the introduced epoxycyclododecane compound is catalytically isomerized in the reaction apparatus within a relatively short time at a high conversion thereof at a high selectivity to the target cyclododecanone compound, and a resultant reaction mixture containing the target cyclododecanone compound at a high yield is continuously collected from the reaction apparatus.

The collected reaction mixture contains the target cyclododecanone compound with a high yield, a small amount of non-reacted epoxycyclododecane compound and the catalyst. The catalyst can be separated from the reaction mixture by a distillation to refine the target cyclododecanone compound.

The resultant cyclododecanone compound has physical and chemical properties (boiling temperature, crystallizing property, and solubility in solvents) very close to those of the starting epoxycyclododecane compound. Therefore, it is very difficult to separate the epoxycyclododecane compound and the corresponding cyclododecanone compound from each other by way of distillation, crystallization and extraction. Thus, the collected cyclododecanone compound preferably contains the non-reacted epoxycyclododecane compound in a content of 5% by mass, or less, more preferably 2% by mass or less, still more preferably 1% by mass or less.

The collected reaction mixture can be practically used as a target cyclododecanone compound product. If necessary, in view of the use, the collected cyclododecanone product can be refined by, for example, distillation to remove the high boiling temperature impurities (by-products).

EXAMPLES

The present invention will be further illustrated by the following examples.

In each of the examples and comparative examples, the isomerization reaction is carried out in a nitrogen gas atmosphere, and the starting reaction mixture containing lithium iodide and epoxycyclododecane was in the state of a homogeneous solution.

Example 1

A glass coiled tube-type reactor as shown in FIG. 3 was employed. The coiled tube 31 of the reactor 30 had a circular cross-sectional profile, an inside radius of 3.2 mm, a length of 3 m and a inside capacity of 97 ml. The coiled tube 31 of the reactor 30 was placed in an oil bath (not shown in FIG. 31) having a temperature of 200° C. A starting reaction mixture comprising 98.6% by mass of epoxycyclododecane and 0.7% by mass (0.97% molar %) of lithium iodide was continuously introduced into the coiled tube 31 through the inlet 32 at a feeding rate of 30 ml/hr by using a fixed displacement pump. The reaction mixture resided in the coiled tube at a temperature of 200° C. for an average residing time of 3.2 hours, and the resultant reaction mixture was collected from the coiled tube through the outlet 33. The collected reaction mixture was cooled to room temperature and then dissolved in toluene. The toluene solution was subjected to a gas chromatographic analysis. In the results of the analysis, no epoxycyclododecane was detected and the content of cyclododecanone was 97.0% by mass. Thus, it was confirmed the conversion of epoxycyclododecane was 100 molar %, and the selectivity to cyclododecanone was 98.4 molar %.

Example 2

The same procedures for producing cyclododecanone as in Example 1 were carried out except that the reaction temperature was changed from 200° C. to 180° C.

The reaction mixture collected from the coiled tube of the reactor was cooled to room temperature and dissolved in toluene. The toluene solution was subjected to a gas chromatographic analysis. In the analysis results, it was confirmed that in the resultant reaction mixture the content of epoxycyclododecane was 1.1% by mass, the content of cyclododecanone was 96.9% by mass, and thus the conversion of epoxycyclododecane was 98.9 molar % and the selectivity to cyclododecanone was 99.4 molar %. In the reactor, the average residing time of the reaction mixture was 3.2 hours.

Example 3

A coiled tube-type reactor-containing reaction apparatus 40 as shown in FIG. 4 was employed. In the reaction apparatus 40, two coiled glass tube reactors 41 and 42 were connected to each other in series. The front coiled glass tube 41a had a circular cross-sectional profile, an inside radius of 3.2 mm, a length of 1.5 m and a capacity of 48 ml. The rear coiled glass tube 42a had a circular cross-sectional profile, an inside radius of 3.2 mm, a length of 1.5 m and a capacity of 48 ml. The outlet 44 of the front tube 41 was directly connected to the inlet 45 of the rear tube 42.

The front coiled tube 41a was placed in a front oil bath having a temperature of 180° C. and the rear coiled tube 42a was placed in a rear oil bath having a temperature of 200° C.

A starting reaction mixture comprising 98.6% by mass of epoxycyclododecane, and 0.71% by mass (0.98 molar %) of lithium iodide was continuously introduced into the front coiled tube 41a through the inlet 43 at a feeding rate of 30 ml/hr, by using a fixed displacement pump, and a resultant reaction mixture was collected from the rear coiled tube 42a through the outlet 46.

The reaction mixture was heated to a temperature of 180° C. in the front coiled tube 41a and to a temperature of 200° C. in the rear coiled tube 42a. The average total residing time was 3.2 hours.

The collected reaction mixture was cooled to room temperature, and dissolved in toluene. The toluene solution was subjected to the gas chromatographic analysis.

In the analysis results, the collected reaction mixture contained 0.001% by mass of epoxycyclododecane and 97.7% by mass of cyclododecanone, the conversion of epoxycyclododecane was 100.0 molar % and the selectivity to cyclododecanone was 99.1 molar %. Also, in the reaction mixture collected from the front coiled tube 41a through the outlet 44, the content of the non-reacted epoxycyclododecane was 3.7% by mass and the conversion of epoxycyclododecane was 96 molar %.

Example 4

An isomerization reaction of epoxycyclododecane was carried out by using a reaction apparatus 70 as shown in FIG. 7 comprising a front coiled glass tube type reactor 71 and a rear vessel type reactor 72 connected to each other in series. The coiled glass tube 72 had a circular cross-sectional profile, an inside radius of 3.2 mm, a length of 1.5 m and a capacity of 48 ml and the rear vessel-type reactor 72 contained 50 ml of a reaction mixture. The front reactor 71 was placed in an oil bath having a temperature of 185° C. and the rear reactor 72 was placed in an oil bath having a temperature of 220° C.

A starting reaction mixture comprising 98.6% by mass of epoxycyclododecane, 0.73% by mass (1.02 molar %) of lithium iodide was continuously introduced, by using a fixed displacement pump at a feeding rate of 30 ml/hr, into the front glass coiled tube 72 through the inlet 73, the introduced reaction mixture passed through the front glass coiled tube 72 at a temperature of 185° C. and then through the rear vessel type reactor 72 at a temperature of 220° C., and the resultant reaction mixture is delivered from the rear reactor 72 by overflowing through the outlet 76, and collected.

The collected reaction mixture was cooled to room temperature and then was dissolved in toluene. The toluene solution was subjected to the gas chromatographic analysis. In the analysis results, the content of the non-reacted epoxycyclododecane was 0.06% by mass, the content of cyclododecanone was 97.4% by mass. From this analysis result, it was calculated that the conversion of epoxycyclododecane was 99.9 molar % and the selectivity to cyclododecanone was 98.9%. In the above-mentioned reaction procedures, the average residing time of the reaction mixture in the reaction apparatus was 3.3 hours.

Also, it was confirmed that in the reaction mixture delivered from the front coiled tube-type reactor, the content of the non-reacted epoxycyclododecane was 1.4% by mass and the conversion of epoxycyclododecane was 98.6 molar %.

Comparative Example 1

Figure 8:
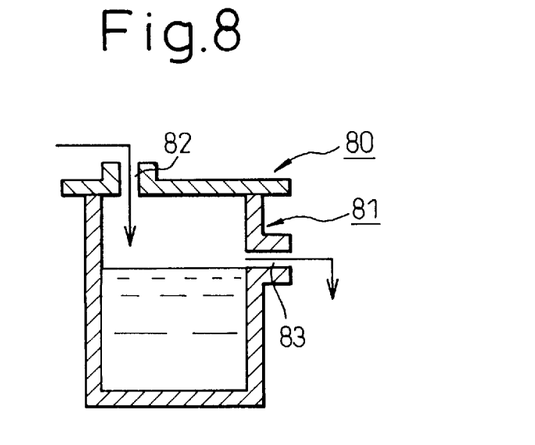
FIG. 8 is an explanatory cross-sectional view of an example of conventional vessel type reactors.

A glass vessel-type reactor having an effective capacity of 100 ml as shown in FIG. 8 was used. In a vessel-type reactor 80 shown in FIG. 8, a closed vessel 81 had an inlet 82 and an outlet 83 and enabled a reaction mixture to be introduced from a supply source (not shown in FIG. 8) into the closed vessel 81 through the inlet 82 and the introduced reaction mixture to be stored in a certain amount in the vessel 81 over a certain time, while being heated by using a heating bath (not shown in FIG. 8) to a certain temperature, and then to be delivered from the vessel 81 by overflowing through the outlet 83.

A starting reaction mixture comprising 98.6% by mass of epoxycyclododecane and 0.73% by mass (1.01 molar %) of lithium iodide was continuously fed, by using a fixed displacement pump at a feeding rate of 30 ml/hr, into the closed vessel 81 through the inlet 82 and then the introduced reaction mixture was heated to a temperature of 200° C. over an average residing time of 3.3 hours in the closed vessel 81, and then the resultant reaction mixture was delivered by overflowing through the outlet 83 and collected. In the vessel 81, the introduced reaction mixture was stirred by using a stirrer piece (not shown in FIG. 8).

After the reaction condition in the vessel 81 was stabilized, the collected reaction mixture was cooled to room temperature and dissolved in toluene. The toluene solution was subjected to the gas chromatographic analysis. In the analysis results, the content of the non-reacted epoxycyclododecane was 3.92% by mass and the content of the resultant cyclododecanone was 91.2% by mass. Thus, it was calculated that the conversion of epoxycyclododecane was 96.0 molar % and the selectivity to cyclododecanone was 96.3 molar %.

Comparative Example 2

The same procedures for the production of cyclododecanone and the same analysis as in Comparative Example 1 were carried out, except that the reaction temperature was changed from 200° C. to 180° C. After the reaction condition in the vessel 81 was stabilized, the collected reaction mixture was cooled to room temperature, and dissolved in toluene. The toluene solution was subjected to the gas chromatographic analysis. In the analysis results, the collected reaction mixture contained 10.7% by mass of non-reacted epoxycyclododecane and 87.1% by mass of cyclododecanone. Thus, the conversion of epoxycyclododecane was 89.1 molar % and the selectivity to cyclododecanone was 99.1%. The average residing time of the reaction mixture in the vessel 81 was 3.3 hours.

Comparative Example 3

Figure 9:
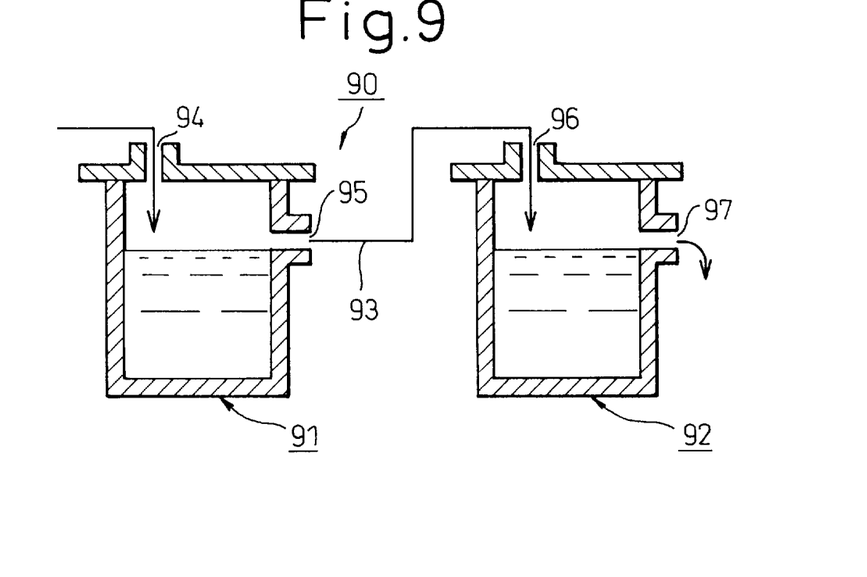
FIG. 9 is an explanatory cross-sectional view of another example of conventional vessel type reactors.

A closed vessel type reactor 90 as shown in FIG. 9 was employed.

In FIG. 9, two closed glass vessels 91 and 92 each having an effective capacity of 50 ml were connected in series to each other through a conduit 93 to provide the reactor 90. The front vessel 91 had an inlet 94 connected to a supply source (not shown in FIG. 9) of a starting reaction mixture and an outlet 95, and the rear vessel 92 had an inlet 96 connected to the outlet 95 of the front vessel 91 through the conduit 93 and an outlet 97. The reactor 90 enabled a reaction mixture to be introduced from the supply source (not shown) into the front vessel 91 through the inlet 94, to be stored in the front vessel 91 in a certain residing time, to be delivered from the front vessel 91 by overflowing through the outlet 95, to be introduced into the rear vessel 92 through a conduit 93 and an inlet 96 of the rear vessel 92, to be stored in the rear vessel 92 for a certain residing time and then to be delivered from the rear vessel 92 by overflowing through the outlet 97.

The front and rear vessels 91 and 92 are separately placed in a front oil bath (not shown) and a rear oil bath (not shown), to separately control the temperature of portions of the reaction mixture contained in the front and rear vessels 91 and 92, to desired levels.

A starting reaction mixture comprising 98.6% by mass of epoxycyclododecane and 0.7% mass (0.97 molar %) of lithium iodide was continuously introduced, by using a fixed displacement pump (not shown) at a feeding rate of 30 ml/hr into the front vessel 91 through the inlet 94, and heated in the front vessel 91 to a temperature of 180° C., the reaction mixture was delivered from the front vessel 91 by overflowing through the outlet 95 and introduced into the rear vessel 92 through the conduit 93 and inlet 96, heated in the rear vessel 92 at a temperature of 200° C. and then delivered from the rear vessel 92 by overflowing through the outlet 97 and the delivered reaction mixture was collected.

In the front and rear vessels 91 and 92, the reaction mixture was stirred by stirring pieces (not shown in FIG. 9). The average total residing time of the reaction mixture in the reaction apparatus 90 was 3.3 hours.

After the reaction condition of the reaction mixture in the reaction apparatus 90 was stabilized, the collected reaction mixture was cooled to room temperature and then dissolved in toluene. The toluene solution was subjected to the gas chromatographic analysis. In the analysis results, the collected reaction mixture contained 1.8% by mass of non-reacted epoxycyclododecane and 94.8% by mass of cyclododecanone. Thus, in the isomerization reaction in the reaction apparatus 90, the conversion of epoxycyclododecane was 98.2 molar % and the selectivity to cyclododecanone was 97.9 molar %. The average total residing time of the reaction mixture in the reaction apparatus 90 was 3.3 hours.

Example 5

Figure 10:
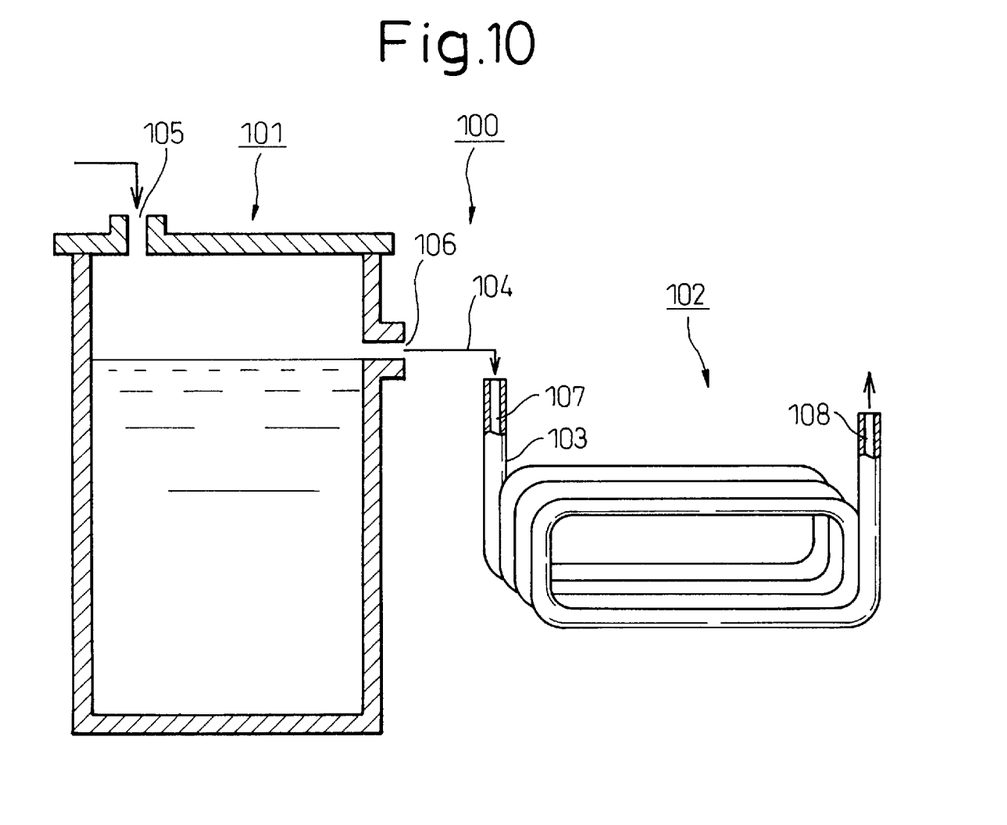
FIG. 10 is an explanatory schematic partial cross-sectional view of a reaction apparatus usable for the method of the present invention.

A reaction apparatus as shown in FIG. 10 was employed.

The reaction apparatus 100 shown in FIG. 10 comprised a front closed vessel type glass reactor 101 having an effective capacity of 240 ml and a rear coiled tube-type glass reactor 102 constituted from a coiled tube 103 having a circular cross-sectional profile, an inside radius of 3.2 mm, a length of 1.5 m and a capacity of 48 ml, connected to the front reactor 101 through a conduit 104.

In FIG. 10, the front vessel type reactor 101 had an inlet 105 connected to a supply source (not shown in FIG. 10) of a starting reaction mixture through a fixed displacement pump (not shown) and an outlet 106 and could contain a certain amount of the reaction medium therein.

In FIG. 10, the coiled tube 103 of the rear reactor 102 had an inlet 107 connected to the outlet 106 of the front reactor 101 through a conduit 104 and an outlet 108.

The reaction apparatus 100 further comprised a front heating bath (not shown) for the front reactor 101 and a rear heating bath (not shown) for the rear reactor 102. The reaction apparatus of FIG. 10 enabled a starting reaction mixture to be continuously introduced from a supply source (not shown) thereof into the front vessel type reactor 101 through the inlet 105; the introduced reaction mixture in the front reactor 101 to be heated by a front heating bath (not shown), to a desired temperature and to be delivered from the front reactor 101 by overflowing through the outlet 106; the delivered reaction mixture to be introduced into the rear reactor 102 through the conduit 106 and the inlet 107; the introduced reaction mixture in the rear reactor 102 to be heated by the rear heating bath (not shown) to a desired temperature and to be delivered from the rear reactor 102 through the outlet 108 and collected.

A starting reaction mixture comprising 98.6% by mass of epoxycyclododecane and 0.73% by mass (1.01 molar %) of lithium iodide was continuously introduced, by using the fixed displacement pump (not shown) at a feeding rate of 30 ml/hr, in an amount of 240 ml into the front reactor 101 through the inlet 105; and the introduced reaction mixture passed through the front reactor 101, while being heated at a temperature of 180° C., and was delivered from the front reactor 101 by overflowing through the outlet 106. The delivered reaction mixture was introduced into the rear reactor 102 through the conduit 104 and the inlet 107; the introduced reaction mixture passed through the coiled tube 103, while being heated at a temperature of 210° C., and then was delivered through the outlet 108 and collected. The total average residing time of the reaction mixture was 9.6 hours.

After the reaction conditions of the reaction mixture in the reaction apparatus 101 was stabilized, the collected reaction mixture was cooled to room temperature and dissolved in toluene. The toluene solution was subjected to the gas chromatographic analysis. In the analysis results, no epoxycyclododecane was detected in the collected reaction mixture and the content of cyclododecanone in the collected reaction mixture was 97.5% by mass. Accordingly, in the above-mentioned isomerization reaction the conversion of epoxycyclododecane was 100.0 molar % and the selectivity to cyclododecanone was 98.9 molar %. Also, it was found that in a portion of the reaction mixture delivered from the front reactor 101, the content of non-reacted epoxycyclododecane was 4.7% by mass and the conversion of epoxycyclododecane was 95.2 molar %.

Comparative Example 4

A vessel-type reactor as shown in FIG. 8 was employed. The reactor had an effective capacity of 300 ml.

A starting reaction mixture comprising 98.6 by mass of epoxycyclododecane and 0.73% by mass (1.01 molar %) of lithium iodide was continuously introduced, by using a fixed displacement pump at a feeding rate of 30 ml/hr, into the reactor 80 through the inlet 82 and the introduced reaction mixture was heated at a temperature of 210° C., while being stirred with a stirrer, and was delivered from the reactor 80 by overflowing through the outlet 83, and collected.

After the reaction conditions in the reactor 80 were stabilized, the collected reaction mixture was cooled to room temperature and then dissolved in toluene. The toluene solution was subjected to the gas chromatographic analysis. As analysis results, in the collected reaction mixture, the content of the non-reacted epoxycyclododecane was 0.83% by mass, and the content of the resultant cyclododecanone was 92.0% by mass. Therefore, in the above-mentioned reaction, the conversion of epoxycyclododecane was 99.2 molar % and the selectivity to cyclododecanone was 94.1 molar %. The average residing time of the reaction mixture in the reactor 80 was 10.0 hours.

The reaction conditions and the analysis results of the examples and comparative Examples are shown in Table 1.

TABLE 1

| | | | Reaction conditions | | | Analysis results | |
| | | | | | | Conversion | |
| | | Type of catalyst | Reaction temperature (° C.) | | Total residing | of epoxy-cyclo- | Selectivity to cyclo- |
| Example No. | Feeding rate (ml/hr) | (Conc. molar %) | Front reactor | Rear reactor | time (hr) | dodecane (molar %) | dodecanone (molar %) |
|---|---|---|---|---|---|---|---|
| Example 1 | 30 | LiI (0.97) | 200 | — | 3.2 | 100 | 98.4 |
| Comparative Example 1 | 30 | LiI (1.01) | 200 | — | 3.3 | 96.0 | 96.3 |
| Example 2 | 30 | LiI (1.01) | 180 | — | 3.2 | 98.9 | 99.4 |
| Comparative Example 2 | 30 | LiI (1.00) | 180 | — | 3.3 | 89.1 | 99.1 |
| Example 3 | 30 | LiI (0.98) | 180 | 200 | 3.2 | 100 | 99.1 |
| Comparative Example 3 | 30 | LiI (0.97) | 180 | 200 | 3.3 | 98.2 | 97.9 |
| Example 4 | 30 | LiI (1.02) | 185 | 220 | 3.3 | 99.9 | 98.9 |
| Example 5 | 30 | LiI (1.01) | 180 | 210 | 9.6 | 100 | 98.9 |
| Comparative Example 4 | 30 | LiI (1.01) | 210 | — | 10.0 | 99.2 | 94.1 |

Table 1 clearly shows that, in accordance with the method of the present invention, a cyclododecanone compound can be continuously produced from a corresponding epoxycyclododecane compound within a relatively short time with a high conversion of the epoxycyclododecane compound and with a high selectivity to the target cyclododecanone compound at a high reaction stability even in a large industrial scale.

What is claimed is:

1. A method of continuously producing a cyclododecanone compound, comprising isomerizing an epoxycyclododecane compound in the presence of a catalyst comprising at least one member selected from the group consisting of lithium bromide and lithium iodide, wherein the isomerization reaction is continuously carried out by passing a reaction mixture comprising the epoxycyclododecane compound and the catalyst through a continuous reaction apparatus comprising at least one tubular reactor in a nonreactive gas atmosphere comprising at least one member selected from the group consisting of helium, neon, argon, hydrogen, nitrogen, methane and ethylene gases.

2. The method of continuously producing a cyclododecanone compound as claimed in claim 1, wherein the epoxycyclododecane compound is selected from saturated and unsaturated cyclohydrocarbon compounds having 12 carbon atoms and an epoxy group.

3. The method of continuously producing a cyclododecanone compound as claimed in claim 1, wherein the epoxycyclododecane compound is selected from epoxycyclododecane, epoxycyclododecenes, epoxycyclododecadienes and epoxycyclododecatrienes.

4. The method of continuously producing a cyclododecanone compound as claimed in claim 1, wherein the continuous reaction apparatus further comprises at least one vessel type reactor connected to the tubular reactor in series.

5. The method of continuously producing a cyclododecanone compound as claimed in claim 1, wherein the catalyst comprises lithium iodide.

6. The method of continuously producing a cyclododecanone compound as claimed in claim 1, wherein the catalyst is present in an amount of 0.01 to 20 molar % based on the molar amount of the epoxycyclododecane compound.

7. The method of continuously producing a cyclododecanone compound as claimed in claim 1, wherein the isomerization reaction is carried out at a temperature of 100 to 350° C.

8. The method of continuously producing a cyclododecanone compound as claimed in claim 1, wherein the isomerization reaction is carried out at a temperature of 100 to 190° C. until the conversion of the epoxycyclododecane compound in the reaction mixture reaches a level of 90 molar % or more.

9. The method of continuously producing a cyclododecanone compound as claimed in claim 1, wherein the isomerization reaction is carried out at a temperature of 100 to 190° C. until the conversion of the epoxycyclododecane compound in the reaction mixture reaches a level of 90 molar % or more and, thereafter, at a temperature of 190° C. to 350° C.

* * * * *